United States Patent [19]

Resh

[11] 4,399,404
[45] Aug. 16, 1983

[54] MOISTURE TESTER WITH PROBE

[76] Inventor: Roy E. Resh, 2729 Sycamore Ter., Bettendorf, Iowa 52732

[21] Appl. No.: 237,368

[22] Filed: Feb. 23, 1981

[51] Int. Cl.³ .......................... G01R 27/26; G01N 5/02
[52] U.S. Cl. ................................ 324/61 R; 324/61 P; 73/73
[58] Field of Search ............... 73/73; 324/61 R, 61 P, 324/DIG. 1, 60 C

[56] References Cited

U.S. PATENT DOCUMENTS

| | | | |
|---|---|---|---|
| 2,468,687 | 4/1949 | Schmitt | 324/111 X |
| 3,141,129 | 7/1964 | Dietert | 324/61 R X |
| 3,862,571 | 1/1975 | Vogel | 324/61 P X |
| 4,174,498 | 11/1979 | Preikschat | 324/61 R X |
| 4,245,188 | 1/1981 | Rottmar | 324/61 P |

*Primary Examiner*—Stanley T. Krawczewicz
*Assistant Examiner*—Jose M. Solis
*Attorney, Agent, or Firm*—Glenn H. Antrim

[57] ABSTRACT

The tester has a probe to be inserted into granular or fluid materials for measuring instantly permittivity and temperature. The characteristics of materials are measured according to permittivity, the characteristics of moisture of grains being used as an example in the present embodiment. Features of the tester include: a sensing capacitor within a tip of the probe being an extension of a printed circuit board mounted within a main casing of the probe, an adjustable printed-circuit type capacitor as a reference in cooperation with the sensing capacitor in a balanced input circuit, touch-type switches to which battery is continually supplied to select instantly different calibrations for different characteristic curves without operation of any other switches, and the use of voltage dividers selected by the switches to provide a voltage for zero crossing and another voltage to adjust gain according to the slope of a desired curve, the voltages from a voltage divider for different gains being varied as a function of temperature at the probe.

5 Claims, 9 Drawing Figures

MOISTURE TESTER WITH PROBE

BACKGROUND OF THE INVENTION

This invention relates namely to testers for measuring moisture in granular materials such as grain, but also relates to fluid level and temperature indicators, and particularly to testers having probes to be readily inserted into granular materials for determining their characteristics by measuring permittivity and temperature.

Commonly, grain moisture testers have containers into which exact amounts of grain are poured. A sample of grain to be measured often fills space between two electrodes for changing electrical capacitance therebetween. The permittivity of the sample is determined from the capacitance between the electrodes in a filled container. Since the permittivities of different samples depend not only upon the amounts of moisture in the samples but also on their temperatures, temperatures of the samples must be measured and be used in the calibration of the instruments for moisture.

Different samples of grain are taken from storage bins, box cars, and barges to be placed in the moisture testers. Small containers attached to rods as handles may be inserted, opened, closed, and withdrawn to provide samples from different points. The quantity of each sample must usually have to be precisely measured in preparation for measuring moisture.

SUMMARY OF THE INVENTION

An electrical tester according to the present invention is particularly suitable for electronically testing quickly characteristics of granular materials while samples being tested are left in place in usual containers for storage or for transportation. A testing probe contains a sensing component and electronic detecting circuits and is inserted by an extensible handle to any position that is accessible within a bulk of fluid material to be tested. The sample to be tested is the material immediately surrounding the tip of the probe, and the detecting circuits provide an output to be converted into a reading of a desired characteristic at the output of the tester. A number of readings can be taken quickly at different points within the material to determine to what extent the material is uniform.

A main casing for the probe is a short piece of metallic cylinder; the extensible handle is connected to one end of the cylinder; and the tip of the probe comprises a dielectric cone having a base attached to the opposite end of the cylinder and an outer point on the axis of the cylinder. Printed circuit conductors within the point of the cone are part of a sensing capacitor. The electronic detecting circuits for providing signals proportional to the capacitance of the sensing capacitor are contained within the cylinder.

The electronic detecting circuits are contained on a printed circuit board that is positioned diametrically within the cylinder. One end of the circuit board has an extending, relatively narrow portion of substrate positioned axially within the cone. A thin layer of conductive material like that commonly used in printed circuits covers each side of the narrow extending portion. Preferably, the thin layers on the circuit board are rectangular and have one end spaced quite closely within the tip of the cone, but still the outer corners of the layers must be spaced a short distance from the inner surface of the cone. The other or inner respective ends of the layers are still spaced a substantial distance beyond the end of the metallic cylinder. The thin layers are connected together to form a single electrode of the sensing capacitor, and the adjacent end of the cylinder functions as its other electrode. When the probe is inserted into material to be tested, such as grain to be tested for moisture content, the material immediately along the wall of the tip is nearly within the most intense portion of the pattern of the electric field between the electrodes of the sensing capacitor, and therefore the permittivity of this adjacent material affects substantially the capacitance of the capacitor.

The electronic detecting circuits of the circuit board include an oscillator and two similar peak detectors. The sensing capacitor is connected in a capacitive voltage-divider circuit, and the voltage-divider circuit is connected across the output of the oscillator. The oscillator signal is coupled through the sensing capacitor to the input of one of the peak detectors for applying to its input a signal voltage proportional to the capacitance of the sensing capacitor. In a similar manner, the input of the other peak detector is connected through a reference capacitor to the output of the oscillator. In order that the reference capacitor be subjected to about the same temperature as the sensing capacitor, it is mounted on that end of the circuit board from which the sensing capacitor extends. The electrodes of the reference capacitor comprise respective thin circular portions of conductive material on opposite sides of the circuit board, and one of the electrodes has radial projections extending from its periphery over the outer margin of the other electrode. Any portion of any of the projections may be readily scraped off for adjusting the capacitance of the reference capacitor to calibrate the circuits for measuring permittivity.

The peak detectors are connected in a bridge-circuit arrangement, and their outputs are applied to respective inputs of a direct-current differential amplifier. The direct-current output of the differential amplifier is fed back to the input of one of the peak detectors as a bias voltage, preferably to the same input to which the sensing capacitor is connected. The bias of the other peak detector is maintained constant from a source of regulated voltage. The voltage that is fed back has the proper polarity to tend to balance the bridge-circuit arrangement, and because of the high gain of the differential amplifier, the outputs of the peak detectors are effectively the same values at all times during their operation. The feed-back voltage developed at the output of the differential amplifier is also applied to the input of another amplifier, and the amplified output is applied to an output terminal of the electronic detecting circuit. This output is proportional to the permittivity of the material being tested and is applied through function switching circuits to an analog-to-digital converter having an output connected to a liquid crystal display.

Temperature readings of the materials being tested are also provided. Temperature readings in themselves are often important, for example, increase in temperature of grains may indicate a condition for spoilage. Also, calibration of moisture readings as derived from permittivity depend upon temperature. In the present instrument, voltages proportional to temperatures are inserted directly for automatic compensation as required to provide direct digital readings of moisture.

A temperature-sensitive diode for supplying temperature readings and compensation is positioned outside a slot in the wall of the cylinder of the probe. The diode is positioned there by having its leads (pigtails) inserted into holes that extend from the edge of the circuit board parallel to its sides until it enters printed-through holes connected to usual printed conductors. The ends of the leads are soldered to the printed-through holes in a usual manner.

A preferred function switching circuit for receiving the outputs of the electronic circuit of the probe provides selection of temperature readings, and humidity readings for corn, wheat, and soybeans. The function switching circuit comprises resistive touch switches, electronic switching circuits, a battery, and resistive voltage dividers to provide calibration for the various functions. The battery is connected at all times to supply the very small amount of current to switching circuits connected to the resistive touch switches. In response to operation of any of the switches, the battery is connected to supply an additional small amount of current required for operating circuits to display desired readings.

In response to the selection of a desired function, the switching circuit connects required resistive voltage-dividers for supplying from the probe and from regulated voltage-biasing circuits proper proportions of voltages to calibrate the tester for permittivity or for temperature to display digitally the desired reading. A feature of the preferred function switching circuit is the use of a simplified voltage-divider circuit for calibration of functions that have characteristic curves that cross. The function switching circuit is connected to a usual analog-to-digital converter connected to a liquid crystal display for moisture and temperature readings.

DESCRIPTION OF THE PREFERRED EMBODIMENT

Figure 1:
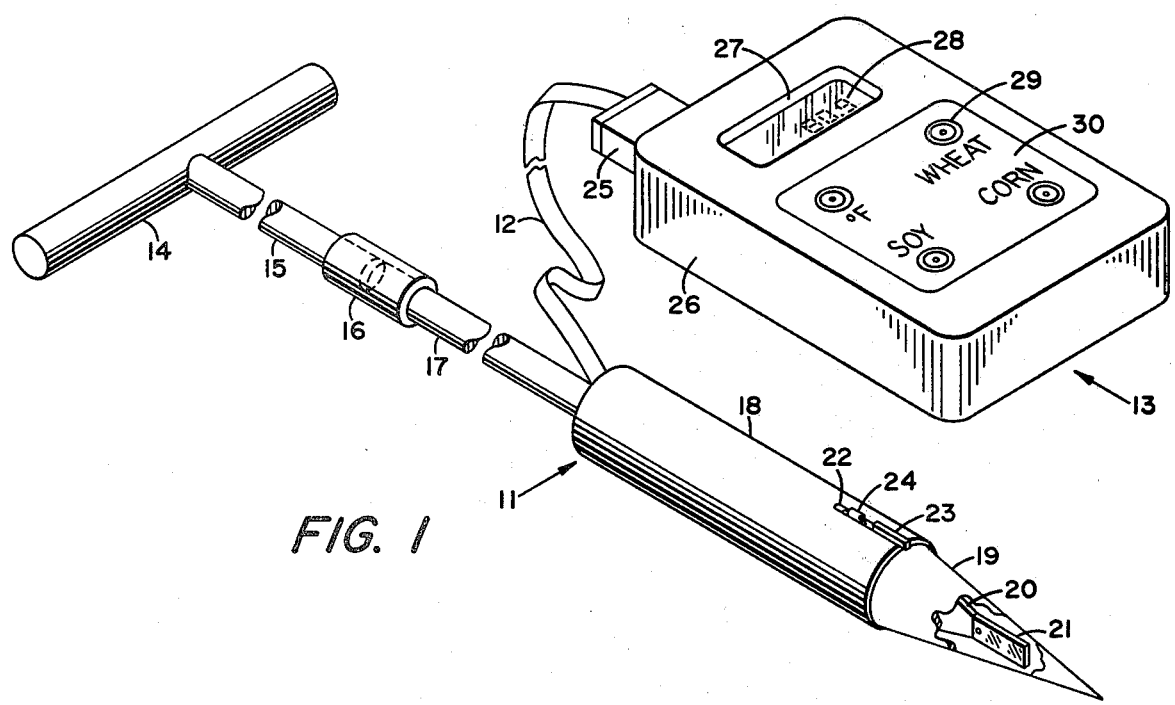
FIG. 1 is a perspective view of the probe and the display circuit of a tester according to this invention for measuring temperature and humidity of grain.

A probe 11 for insertion into granular materials is shown in FIG. 1 connected through a cable 12 to a display assembly 13 for displaying temperature reading and moisture content of soybeans, wheat, and corn. An extensible handle of the probe 11 comprises a transverse grip 14, a piece of rod 15 of moderate length having one end connected to the grip and another to a pipe coupling 16, an extension rod 17 of somewhat greater length with opposite threaded ends attached to the coupling 16 and to an end of a piece of conductive cylindrical tubing 18. The cylindrical tubing 18 is the main casing of the probe, and the extension rod 17 is turned into a disk (not shown) within the end of the cylinder. When the probe 11 is to be inserted only short distances into granular materials to be tested, an extension need not be used, and the rod 15 of the handle can be attached directly to the disk within the end of the cylinder 18.

The cylinder 18 is the main portion of the casing for the probe 11 and may be made of steel, and the rest of the casing is a pointed dielectric cone 19 fabricated from polystyrene. The base of the cone 19 snaps securely to the end of the tubing 18 opposite that end to which the handle 14 is attached. A printed circuit board 20 is mounted diametrically within the tubing 18, and a more narrow rectangular portion 31 (FIG. 4) of the substrate of the circuit board extends axially toward the point of the cone 19. As described below, an electrode of a sensing capacitor 21 is formed by thin plates of deposited metallic conductive material on the sides of the projecting rectangular portion.

The circuit board 20 extends a substantial distance into the tubing 18, the width of the circuit board generally being slightly less than the inside diameter of the tubing 18, and a portion extending beyond the end of the tubing 18 is gradually decreased to the width of the rectangular portion 31 for the sensing capacitor 21. The short portion of the printed circuit board 20 that is just within the end of the tubing 18 is extended outwardly somewhat to form at each side a tab 23, and the end of the tubing 18 has diametrically opposite slots 22 of sufficient length in an axial direction to receive the tabs 23 as the circuit board 20 is pushed into the tubing 18. One of the slots 22 is substantially longer than the tabs 23 to receive a temperature sensitive diode 24 spaced a short distance from the inner end of one of the tabs 23.

The cable 12 between the probe 11 and the display assembly 13 comprises a required number of plastic insulated conductors side by side connected through a usual plug 25 to circuits of the display assembly 13. A rectangular metallic case 26 for the display assembly 13 has a window 27 over a liquid crystal display 28 and a touch switch 29 for each of four functions for obtaining readings of temperature and of humidity for wheat, corn, and soybeans. The case 26 and a plate on which the functions are indicated are metallic and are connected to ground as a return circuit for the touch switches 29. Each of the touch switches 29 may simply be threaded screws that extend through an inside circuit board (not shown) for the electronic circuits of the display assembly 13 and into inside-threaded, insulating shoulder washers about each of the holes for each of the switches 29 within the case 26. A metallic tab about each of the screws on the printed circuit board for the display assembly 13 is connected to the printed circuitry for the display assembly 13 such that the screws function both as electrical, conductive portions of the touch switches 29 and as mounting screws for the circuit board within the case 26.

Figure 2:
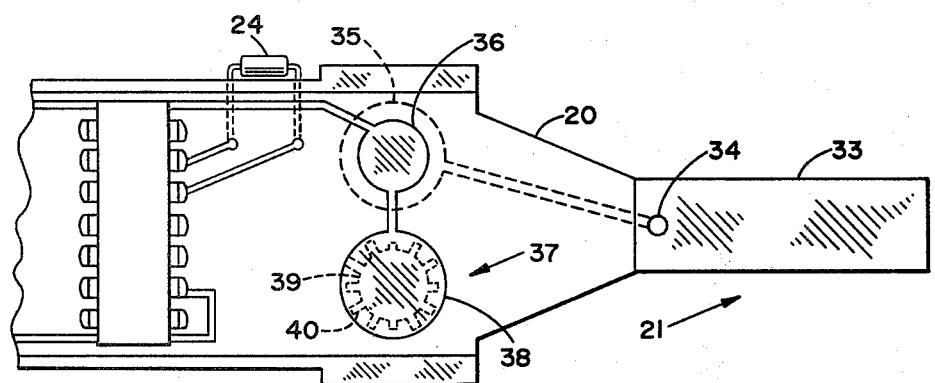
FIG. 2 is a view of a side of an end portion of a printed circuit board showing a sensing capacitor to be positioned inside the probe.
Figure 3:
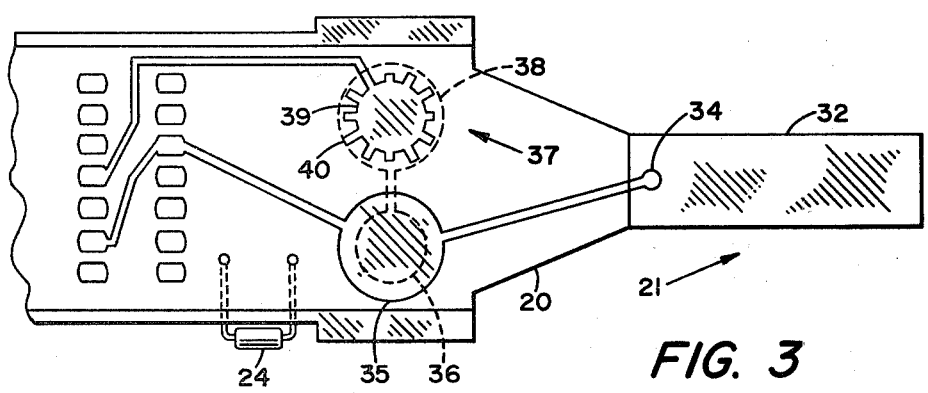
FIG. 3 shows the opposite side of the end portion of the printed circuit board of FIG. 2.
Figure 4:
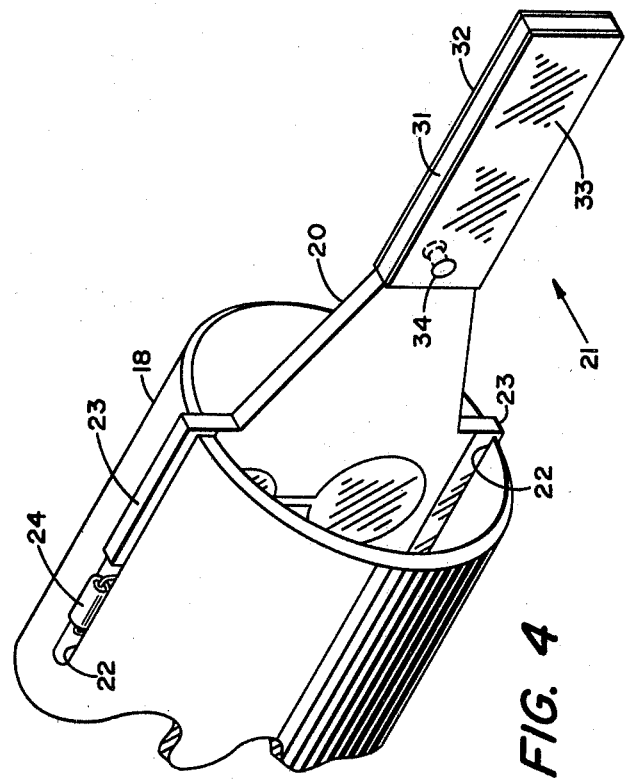
FIG. 4 is a perspective view of an end of the probe to show the mounting of a temperature sensing diode.

The construction of the end of the circuit board 20 having the sensing capacitor 21 is shown clearly in FIGS. 2-5. As shown in FIG. 4, the substrate of the circuit board 20 has an axially extending, rectangular portion 31, and each of the opposite sides of the rectangular portion of the substrate has a thin layer of conductive material 32 or 33. These thin layers are connected together to form one electrode of the sensing capacitor 21. The other electrode of the sensing capacitor 21 is the adjacent end of the cylinder 18, the cylinder being a part of a common return circuit referred to as ground. Typically, each of the thin conductive layers 32 and 33 may be about 1-inch (25.4 mm) long and about ¼-inch (6.35 mm) wide. The inner ends of the thin layers 32 and 33 may be about ⅞-inch (22.2 mm) in an axial direction from the adjacent end of the tubing 18. Although for greatest sensitivity, the outer end of the thin layers 32 and 33 must be quite close to the inner surface of the wall of the dielectric cone 19, still a small space must be maintained in order to avoid erroneous readings for average amounts of moisture resulting from occasional granules with greater than average amounts of moisture being close to the layers 32 and 33 of the sensing capacitor 21.

The thin layers 32 and 33 that comprise one electrode of the sensing capacitor 21 are connected together and coupled to an input of a peak detector, described below, through a coupling capacitor that comprises opposite, circular thin layers 35 and 36 (FIG. 3) of conductive material on the substrate of the circuit board 20. In more detail, the thin layers 32 and 33 of the sensing capacitor 21 are connected together by a printed-through hole 34 that is also connected to a conductor extending to the round thin layer or electrode 35 on one side of the circuit board 20. The thin layer or electrode 36 on the opposite side of the board is somewhat smaller in diameter and is connected to succeeding circuits.

As described in detail below with reference to FIGS. 6 and 7, the sensing capacitor 21 is connected to one input of a bridge circuit including a peak detector 46, and a reference capacitor 37 is connected in another input of a bridge circuit including another peak detector 47. On the side of the circuit board 20 shown in FIG. 2, the reference capacitor 37 has a round electrode 38 of conductive printed-circuit material, and on the opposite side shown in FIG. 3, has an electrode with a solid portion 39 of smaller diameter centered over the opposite electrode 38 and has spaced radial projections 40 extending outwardly over the margin of the electrode 38. Any of the projections or any portion thereof can be readily removed by scraping with a sharp edge to adjust the capacitance of the reference capacitor 37. The output of the electronic circuit of FIGS. 6 and 7 are calibrated or balanced by adjusting the capacitance of the capacitor 37 to provide zero output for permittivity while the probe is not in use.

Figure 5:
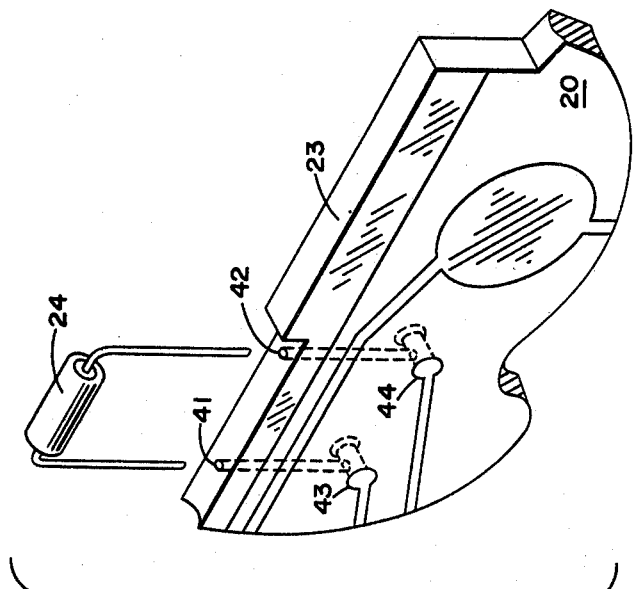
FIG. 5 is a perspective view of a fragmentary portion of the circuit board to show means for mounting the diode.

The temperature-sensitive diode 24 is mounted to the edge of the substrate of the printed circuit board 20 as shown in FIGS. 4 and 5 by inserting leads or pigtails of the diode into holes parallel with the sides of the printed circuit board. Parallel holes 41 and 42 spaced a short distance apart from the tab 23 are drilled into the board to enter printed-through holes 43 and 44 respectively. The distance between the holes 41 and 42 is somewhat greater than the length of the diode 24 such that its pigtails can be turned at right angles near the respective ends of the diode for inserting the pigtails into the holes. Pigtails have been cut to the proper length such that their ends enter the respective printed-through holes 43 and 44 as the diode is positioned close to the edge of the substrate of the printed circuit board 20. Conductors of the printed circuit board are connected in the usual manner to the printed-through holes 43 and 44 and the ends of the pigtails are soldered at the holes to the conductors. When the circuit board 20 is inserted within the cylinder 18, the diode 24 will be exposed to be in contact with the material that is being tested.

Figure 7:
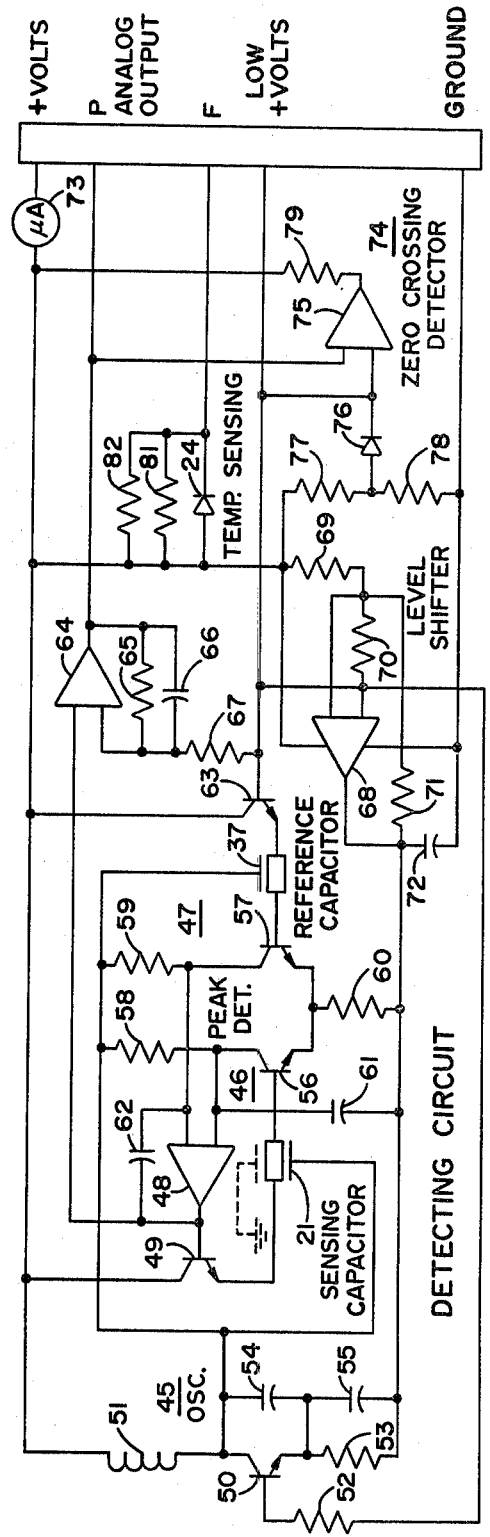
FIG. 7 is a schematic diagram of the circuits for the probe.

The electronic circuit of the printed circuit board 20 supplies two precisely controlled values of direct-current voltage at the output terminals marked P and F, respectively as shown in FIG. 7. The voltage at the terminal P is determined by the sensing capacitor 21 as a function of permittivity of material into which the probe 11 is inserted, and the voltage at the terminal F is determined by the resistance of the diode 24 as affected by temperature of the material and also by values of selected resistors in the function switching circuit shown in FIGS. 8 and 9.

Figure 6:
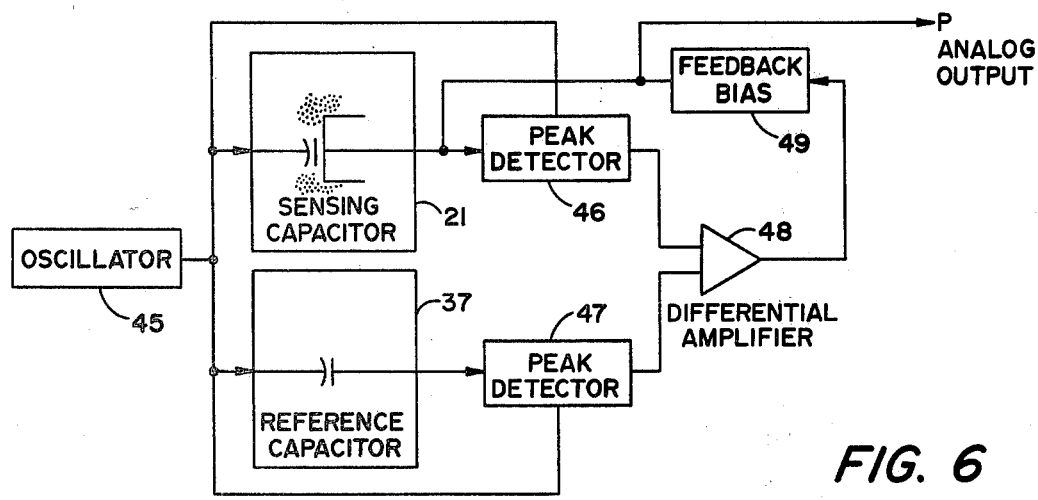
FIG. 6 is a simplified block diagram of the circuits of the printed circuit board for the probe.

The circuit for supplying voltage for permittivity at the output or analog terminal P as a function of the value of the sensing capacitor 21 is shown in simplified form in FIG. 6. An oscillator 45 applies signal through the sensing capacitor 21 and the reference capacitor 37 to the input of a peak detector 46 and the input of a peak detector 47 respectively. The sensing capacitor 21 and the reference capacitor 37 are part of respective capacitive voltage divider circuits for supplying to the peak detectors 46 and 47 respectively voltages proportional to the values of the respective capacitors 21 and 37. The outputs of the peak detectors 46 and 47 are connected in a bridge-circuit arrangement with intermediate diagonal points being connected to respective inputs of the high gain differential amplifier 48. The peak detectors 46 and 47 are conductive only while signals applied to the respective inputs are maximum or near maximum for providing direct-current inputs to the differential amplifier 48.

The output of the differential amplifier 48 is connected through a feedback bias circuit 49 to the input of the peak detector 46 for applying voltage that tends to equalize the outputs of the peak detectors 46 and 47. Because of the high gain of the differential amplifier 48, the difference in voltage between the outputs of the peak detectors 46 and 47 remains effectively zero, and therefore the direct-current voltage developed at the output of the feedback bias circuit 49 is effectively the difference between the peaks of the voltages applied to the peak detectors 46 and 47, the voltage being applied from the capacitive divider circuits including the sensing capacitor 21 and the reference capacitor 37 respectively. Therefore, this direct-current voltage that is applied from the feedback bias circuits 49 to the input of the peak detector 46 is also the voltage that is applied to the output terminal P of the electronic circuits contained within the probe 11. In order to reduce noise, the peak detectors 46 and 47 receive their operating voltages from the output of the oscillator 45.

The complete schematic diagram FIG. 7 includes in addition to the circuits shown functionally in FIG. 6 for measuring a wide range of permittivity, a voltage regulating circuit, a temperature sensing circuit, and a circuit including a zero-crossing detector 74 and the microampere indicator 73. The zero-crossing detector operates in response to a predetermined change in permittivity to provide a substantial change in display on the indicator 73. The oscillator 45 has a transistor 50, and inductor 51, resistors 52 and 53, and capacitors 54 and 55. The values of the resistors 52 and 53 are 39K and 15K ohms respectively and the values of the capacitors 54 and 55 are 20 and 30 picofarads respectively.

The oscillator 45 is a modified Hartley oscillator operating at a typical frequency of 1 megahertz.

The peak detectors 46 and 47 have similar field-effect transistors 56 and 57 with their respective collectors connected through 470K resistors 58 and 59 to the output of the oscillator 45. By being connected in this manner, the output of the oscillator 45 functions as a gating voltage to cause the transistors 46 and 47 to conduct for very short periods to decrease noise. The emitters of the transistors 46 and 47 are connected to a common return circuit through a common 470K resistor 60. The 500-picofarad capacitors 61 and 62 connected to the collectors of the transistors 56 and 57 respectively filter the output to provide direct-current voltage to input terminals of the high gain differential amplifier 48.

The feedback bias circuit 49 of FIG. 6 essentially comprises a transistor 49 connected as shown to apply output from the differential amplifier 48 to the base of the transistor 56 to balance the peak detectors 46 and 47 as described above. The electrode of the sensing capacitor 21 shown connected to the base of the transistor 56 and to the emitter of the transistor 49 comprises both the inter-connected thin layers of conductive material 32 and 33 shown in FIG. 4 and the electrode 35 shown in FIG. 3. The electrode 36 of the capacitor 21 as shown in FIGS. 2 and 3 is the electrode shown connected directly to the output of the oscillator 45. The dashed line for an electrode of the capacitor 21 shown in FIG. 7 represents the end of the cylinder 18.

The electrode of the reference capacitor 37 of FIG. 7 connected to the base of the transistor 57 is that electrode of FIGS. 3 and 4 having a solid circular portion 39 with removable projections 40. The opposite electrode 38 is connected to the output of the oscillator 45. The inherent capacitance of the transistor 57 completes the capacitive bridge to ground. If required, for example when the oscillator 45 operates at a lower frequency, an additional insulated film or plate may be attached over the solid portion 39 and connected to ground. The stability of the portion of the bridge circuit including the peak detector 47 and the reference capacitor 37 with respect to the capacitive sensing circuit 46 is good, because the reference capacitor is positioned adjacent the sensing capacitor as shown in FIGS. 4 and 5 to have the same temperature, and the biasing circuit for the base of the transistor 57 receives its biasing voltage from the terminal for regulated low voltage through the emitter circuit of the transistor 63.

The amplified direct-current feedback voltage from the output of the amplifier 48 is applied to an input of a high gain amplifier 64, and the output of the amplifier 64 is applied to the P output terminal for application through switching circuits to the analog-to-digital converter. A feedback circuit between the output and the input of the amplifier 64 for filtering out any small variations comprises a parallel 1-megohm resistor 65 and a capacitor 66 of 0.05 microfarad capacitance. This input of the amplifier 64 is also connected through a 27 K-ohm resistor 67 to the source of regulated low voltage.

Figure 9:
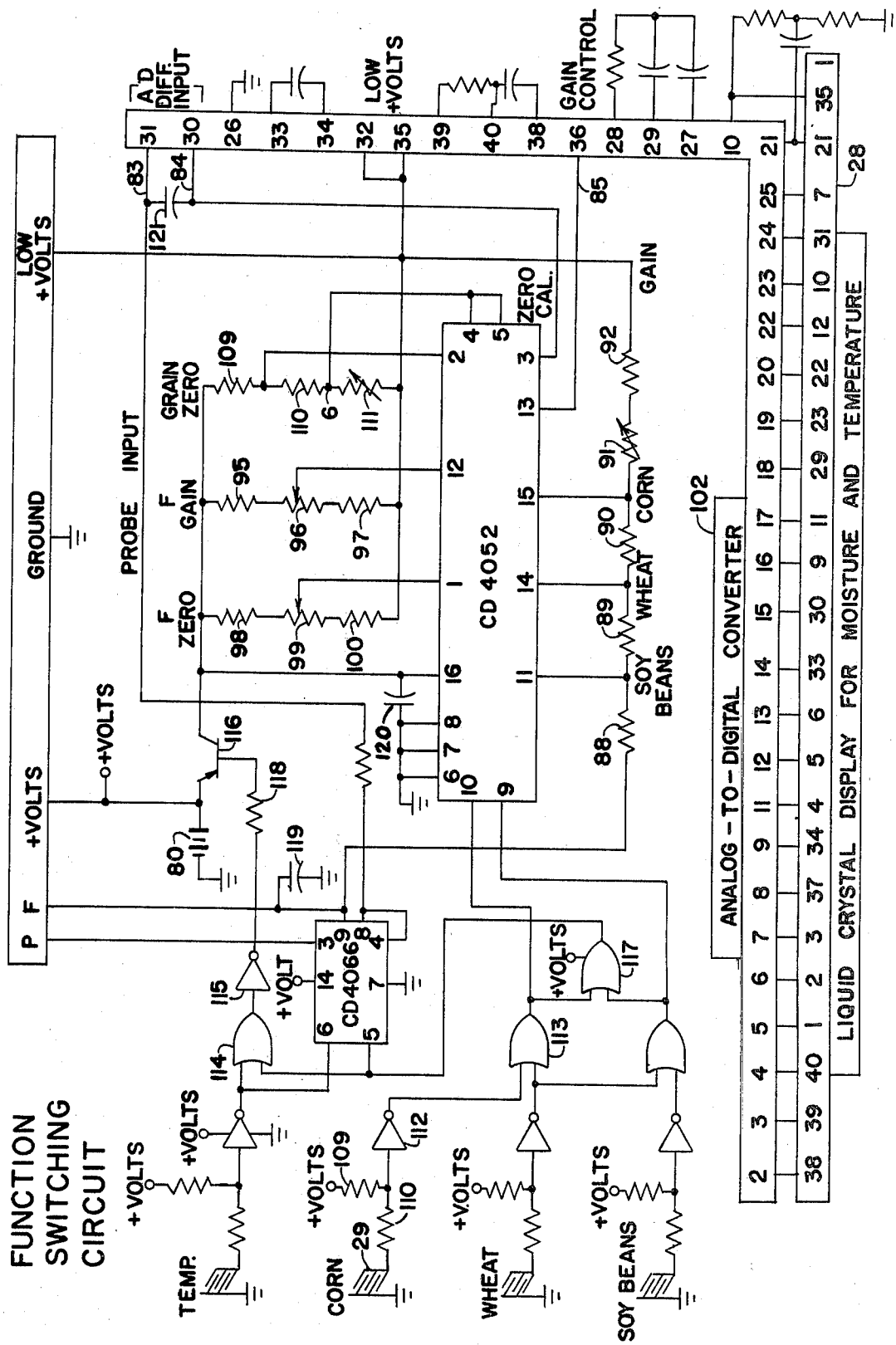
FIG. 9 is a schematic diagram of the function switching circuits with outputs connected to an analog-to-digital converter for connection to circuits of a liquid crystal display.

The power for all of the electronic circuits of the tester is supplied from a 9-volt battery 80 shown in connection with the function switching circuits of FIG. 9. The operation of the detecting circuits that supply signal voltage to the output terminal P is stabilized by a regulator within the analog-to-digital converter 102 and by a level shifter having a two-input amplifier 68. The regulator within the converter 102 very closely regulates the + low volts connected to the connector of FIG. 7 with respect to + volts of that connector. The return circuits of the oscillator 45 and the peak detectors 46 and 47 are connected to the output of the amplifier 68 rather than directly in the usual manner to ground. One input terminal of the amplifier 68 of the level shifter is connected directly to the terminal for + low voltage and the other input terminal of the amplifier 68 is connected to an intermediate point of a voltage divider comprising 39 K-ohm resistors 69 and 70 connected between the terminals for + volts and low voltage. The constant gain of the amplifier 68 is provided by a 47 K-ohm resistor 71 connected between the input that is connected to the intermediate point of the voltage divider and the output of the amplifier 68. The return line that is connected to the output of the amplifier 68 has a capacitor 72 connected to ground as a return for a-c signals.

When the tester is fully utilized to measure temperature and permittivity over a continuous range, five conductors are required in the cable 12 between the probe 11 and the display assembly 13, but in a mode of operation for testing only level of material in a bin, only two conductors are required for operating a zero-crossing detector 74 and a microampere indicator 73 as shown in FIG. 7. When the probe 11 is positioned at a particular level in a bin, the probe will sense an abrupt, substantial change in permittivity when the level of material rises either above or below that particular point. In order for the circuits of FIG. 7 to operate for showing a substantial change in current through the microampere indicator 73, only a main source of voltage, for example, a 9-volt battery, need be connected between the ground terminal and the + volt terminal of the connector of the probe 11. The microampere indicator 73 is connected in the lead that supplies current to all the circuits of FIG. 7 from the + volt terminal.

The zero-crossing detector 74 comprises an amplifier 75 having one input connected to the output of the amplifier 64 that supplies direct-current signal as a function of permittivity. The other input of the amplifier 75 is connected to the low-volts terminal to which low voltage is applied as required for measuring a full range of permittivity, and the application of this voltage to the amplifier makes it non-conductive. When only two conductors are connected as required for measurement of level only, this input of the amplifier 75 is connected through a diode 76 to a voltage divider comprising 100 K-ohm resistor 77 and 150 K-ohm resistor 78. This voltage divider is connected effectively across the main source of voltage, such as a 9-volt battery, and the intermediate voltage applied through the diode 76 to the input of the amplifier 75 is lower than that normally supplied from the low-voltage terminal when it is connected for full-range operation. This lower voltage enables the amplifier 75 to become conductive in response to the application to its other input of voltage from the output of the amplifier 64 when this voltage is above a predetermined value for certain permittivity. The output of the amplifier 75 is connected through a 2.2 K-ohm resistor 79 to the terminal of the microampere indicator 73 that is connected to the main supply leads of the rest of the detecting circuit. During this mode of operation, the lower unregulated bias voltage from the resistors 77 and 78 is also supplied for controlling the voltage on the return circuit of the oscillator 45 and the peak detectors 46 and 47; this unregulated lower bias voltage is satisfactory when detecting a substantial change about an approximate predetermined level rather than providing precise readings over a wide range.

The portion of the temperature sensing circuit within the probe 11 comprises parallel temperature sensitive diode 24 and resistors 81 and 82 connected from the + volts supply line to a terminal F at the output of the probe. The temperature sensing circuit is completed through a voltage divider in the function switching circuits of FIGS. 8 and 9 as described below.

Figure 8:
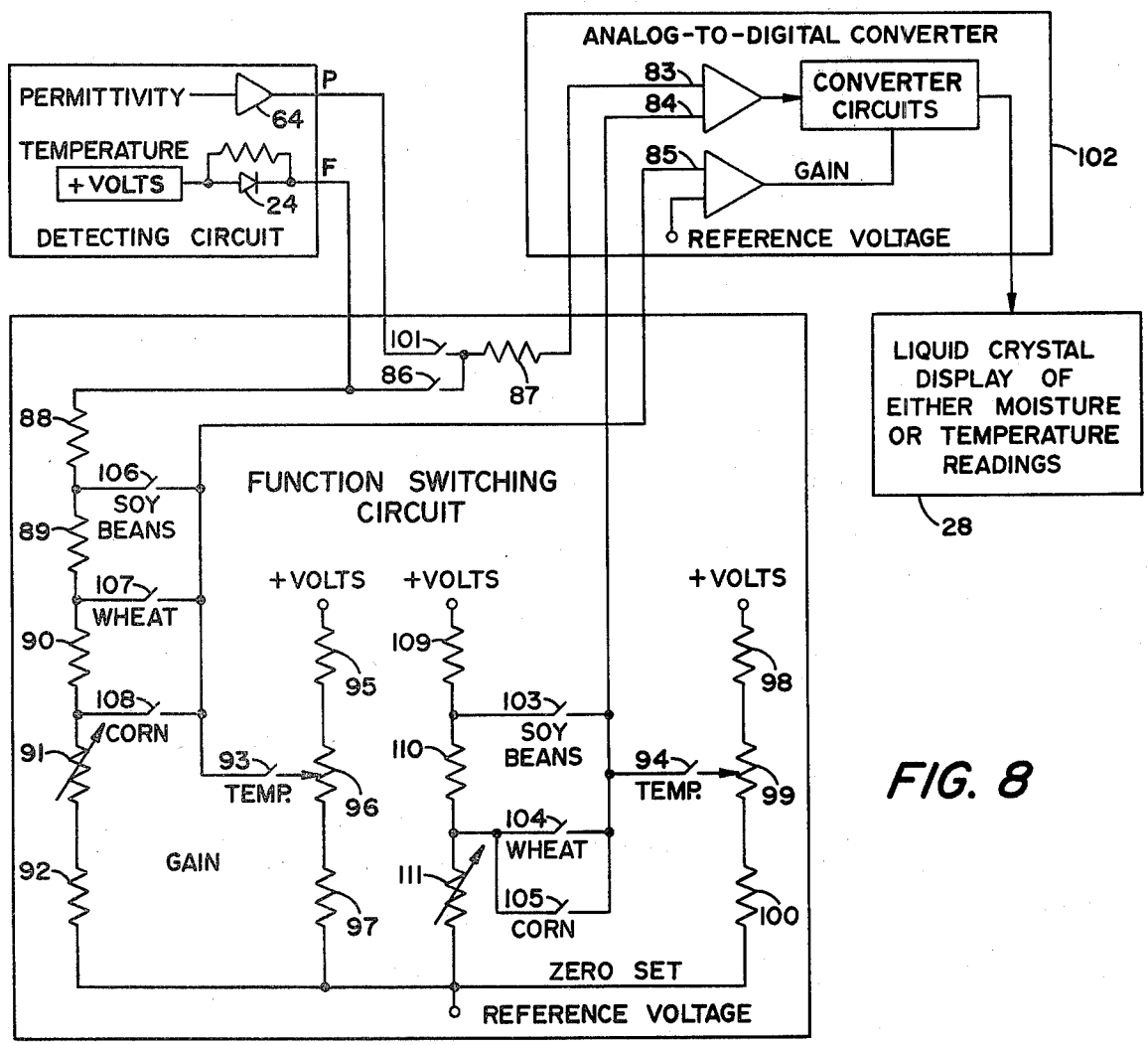
FIG. 8 is a simplified block diagram of the function switching circuits and display circuits connected to output of the circuits within the probe.

The function switching circuits of FIG. 9 can be more easily understood with reference to the simplified diagram of FIG. 8. The direct-current signal voltage for permittivity applied from the P output terminal of the detecting circuit of FIG. 7 and the direct-current signal voltage for temperature applied from the terminal F are applied to switching and voltage dividing circuits of the function switching circuit. Voltages from the function switching circuit are applied to three different inputs of the analog-to-digital converter 102 for determining digital voltages to be applied to the display. The inputs 83 and 84 function differentially such that output of the converter is proportional to the differences of the simultaneously applied voltages, the main signal voltage being applied to the input 83. With respect to curves of characteristics that are to be measured, the voltages for different characteristics applied to the terminal 84 may be termed a zero-set voltage for it determines where the curves of the respective characteristics when extrapolated cross a reference zero line. Voltages applied to an input 85 control gain for determining amplification of the difference of the respective voltages applied to the terminals 83 and 84 and therefore are selected to obtain outputs according to the slopes of selected characteristic curves.

When temperature of materials into which the probe 11 is inserted is to be measured, the switch 86 is closed to apply voltage determined by the resistance of the temperature-sensitive diode 24, through the 100k-ohm resistor 87 to the input terminal 83 of the converter 102. The parallel circuit including the diode 80 and the resistors 81 and 82 is in series with voltage dividing resistors 88-92 that are connected to the regulated low + volts, the resistors not only determining voltage for temperature being applied to the input 83 but also determining voltages applied to the terminal 85 for controlling gain according to required calibrations for measurement of moisture in selected grains. Typical values of the resistors are: resistor 88, 39K ohms; resistor 89, 470 ohms; resistor 90, 1K ohms; variable resistor 91, 1K ohms; and resistor 92, 10K ohms. The values of the resistors have been determined to provide slopes of curves for different permittivity-moisture curves of the grains to be selected. Only resistor 91 needs to be variable to be adjusted according to differences in characteristics of the diodes 24 and values of other components. Simultaneously with the operation of the switch 86 as temperature measurement is selected, the switch 93 operates to supply a fixed voltage to the input 85 for determining gain, and the switch 94 operates to apply a required zero-set voltage to the input 84. The voltage divider for applying voltage to the input 85 comprises: resistor 95, 39K ohms; potentiometer 96, 1K ohms; and resistor 97, 1K ohms; and the divider for applying gain voltage to the input 84 comprises: resistor 98, 10K ohms; potentiometer 99, 1K ohms; and resistor 100, 39K ohms. All the voltage dividers are connected between the regulated + volts and the + low volts.

While any switch of FIG. 1 for selecting humidity measurement for any grain, such as touch switch 29 for corn, is operated, the switch 101 is operated to connect direct-current or analog signal voltage for permittivity from the terminal P of the detecting circuits to the input 83 of the analog-to-digital converter 102. Simultaneously, one of the three switches 103-105 is operated to apply a biasing voltage for zero set to the input 84, and one of the three switches 106-108 is operated to apply a temperature-compensated biasing voltage to the input 85 for controlling gain.

The biasing voltage applied through one of the switches 103-105 is derived from a voltage divider comprising a 1-megohm resistor 109, a 1K-ohm resistor 110, and a 1K-ohm variable resistor 111 connected in series. When a switch 103 for soybeans is operated in response to operation of a touch switch, voltage developed at the junction of resistors 109 and 110 is applied to the input 84, and when a touch switch for either wheat or corn is operated, one of the parallel switches 104 and 105 is operated to apply a somewhat lower voltage from the junction of the resistors 110 and 111. The same voltage is used for wheat and for corn because the curves for moisture as a function of permittivity cross when the moisture contents of the grains are relatively low. Therefore, the curves are extended from this crossover along a line having an average slope of the two curves to provide a common zero.

Different gains for the different slopes of the curves for all three grains are provided by applying different voltages from the voltage divider comprising resistors 88-92. One of the switches 106-108 for soybeans, wheat, and corn respectively and one of the switches 103-105 for the same grain are operated simultaneously with the operation of the switch 101. Operation of each of the switches 106-108 applies a different voltage from the voltage divider comprising resistors 88-92 to the input 85 for controlling gain.

With particular reference to FIG. 9, each of the touch switches, such as the touch switch 29 for corn, is in a resistive circuit that can be traced from the positive terminal of a 9-volt battery 80, through a 10-megohm resistor 109, a 1-megohm resistor 110, and touch switch 29, when it is closed by the tip of a finger, to ground. Each of the converters 112 are biased for nonconduction until a respective touch switch is closed by a tip of a finger. The junction of the resistors 109 and 110 is connected to the input of an inverter 112, and the output of the inverter is connected to an input of an OR gate 113. The other touch switches are likewise connected to inputs of inverting amplifying circuits 112 having outputs connected to OR gates as shown for operating integrated switching circuits CD4066 (two switches of a quad bilateral switch being used) and CD4052 (dual 4-channel analog multiplexer/demultiplexer) to provide the switching described for FIG. 8.

The battery 80 is continually connected to the inverters 112 to prepare them for operation in response to operation of one of the touch switches 29. Until a touch switch is operated, the current drain on the battery 80 is only one microampere to provide nearly shelf life for the battery. When the touch switch for temperature is operated, an OR gate 114 operates to apply voltage through an inverter 115 to the base of a transistor 116 for making it conductive for applying voltage from the battery 80 to the remaining circuits of the tester. When all the circuits are connected, the current drain is still only ten microamperes for the periods that the touch switches 29 are momentarily operated to obtain readings. When any of the touch switches 29 is operated for measuring humidity of corn, wheat, or soybeans, an OR gate 117 operates to operate the OR gate 114 and the transistor 116.

The four inverters corresponding to the inverter 112 and the inverter 115 may be in an integrated circuit such as type 4069, and the four OR gates shown in FIG. 9 may be in an integrated circuit such as type No. 74C32. The value of a resistor 118 connected between the output of the inverter 115 and the base of the transistor 116 is 10K ohms. Filtering is provided by the following 0.05-mfd capacitors: capacitor 119 connected between the input terminal F and ground, capacitor 120 connected between the collector of the on-off transistor 116 and ground, and capacitor 121 connected between the differential high and low inputs 83 and 84 of the analog-to-digital converter 102. The numbers for the terminals of the analog-to-digital converter 102 are those for the type ICL7106A/D converter manufactured by Intersil, Inc. of Cupertino, California. The liquid crystal display 28 is a usual type operated from the analog-to-digital converter 102.

The probe 11 and the display 13 may be connected together during their calibration, but preferably when they are manufactured in quantity, the connectors used for interconnecting the units are connected to respective test circuits for providing standard impedances. For either method, two samples of granular material having different known permittivities and two different standard temperatures are available. Voltages are accurately measured from required test points to the terminal for low + volts.

The following procedure for calibration is described as if the probe 11 and the display 13 were connected together. A similar procedure for separate testing may be used when either the probe or the display are simulated standard circuits. The variable resistor 91 in the voltage-divider in series with the sensing diode 24 is set at about mid-range, and the probe 11 is inserted into granular material held at a predetermined temperature that is somewhat toward the higher end of the range of temperatures that are to be measured by the tester. A voltmeter is connected between the terminal connected to low + volts at the output of the probe and the terminal F connected to the sensing diode 24. The resistors 81 and 82 in parallel with the sensing diode 24 are then selected to provide a predetermined voltage reading that is typical for a properly operating tester. An incorrect reading on the display is now noted and the probe is inserted into granular material having a lower temperature. The actual difference between the temperatures of the two granular materials is substracted from the noted incorrect reading for obtaining a desired second reading to provide a correct difference. The potentiometer 96 in the gain control circuit for temperature is then adjusted to obtain the second reading, and finally the potentiometer 99 in the zero-set circuit for temperature is adjusted for the correct actual reading.

The reference capacitance 37 of the probe is adjusted first when calibrating for moisture measurements. A voltmeter is connected between the terminal for low + volts and the terminal for P output of the probe. While the probe is removed from dielectric materials, the projections 40 of the electrode 39 are gradually scraped away to adjust the capacitance of the reference capacitor 37 to obtain zero reading on the voltmeter. The probe 11 is then inserted into granular material to represent grain having a relatively low moisture content, and a display reading is noted. Then the probe is inserted into a mixture representing grain of higher moisture content, and the variable resistor 91 is adjusted to obtain a new reading that differs from the previously noted reading by an amount equal to the difference in actual permittivity for the two different granular materials. While the probe is still in the granular material for providing a standard reading, the variable resistor 111 for zero-set is adjusted to obtain the correct reading on the display.

The testing described in detail for measuring moisture of grain and for measuring temperature is an example of a tester calibrated for these functions by using the sensing capacitor 21 of this invention for measuring permittivity. A probe having the sensing capacitor of this invention may be used with other electronic circuits calibrated to measure characteristics that vary with permittivity.

I claim:

1. An electronic tester having a detecting circuit and probe, said probe to be inserted in fluid materials to determine permittivities thereof by capacitive measurements, said probe comprising:
   a length of conductive tubing having an end to be inserted into said fluid materials,
   a thin substrate of a printed circuit board, an end of said substrate being disposed diametrically within said end of said tubing and extending axially outward beyond said end of said tubing, a first thin layer of conductive material on said substrate, a maximum transverse dimension of said first thin layer of conductive material being substantial but being less than that of said tubing, said thin layer of conductive material and said end of said conductive tubing forming a sensing capacitor having capacitances determined by different permittivities of materials into which said probe is inserted, and
   said detecting circuit having an input circuit connected to said sensing capacitor and an output providing signals having intensities according to respective permittivities of said materials into which said probe is inserted.

2. An electronic tester as claimed in claim 1 wherein said sensing capacitor has a second thin layer of conductive material, said first and second thin layers being disposed one opposite the other on respective sides of said substrate, and said first and second thin layers being connected together through said substrate.

3. An electronic tester as claimed in either claim 1 or claim 2 wherein said input circuit is bridge-type circuit having first and second legs, said first leg including a first capacitor connected to said sensing capacitor, said second leg including a second capacitor as a reference with respect to said sensing capacitor, each of said first and second capacitors comprising first and second opposite thin conductive layers on respective opposite sides of said substrate, said first layer of at least one of said first and second capacitors having a solid area substantially within the projected perimeter of said second layer of said one capacitor and having spaced projections from the periphery of said solid area extending outwardly over the margin of said second layer of said one capacitor, said projections being easily removable in any required amounts for adjusting said one capacitor.

4. An electronic tester as claimed in claim 1 wherein said conductive tubing is round, a conical cover of plastic material having a base attached to said end of said tubing and a conical wall extending quite closely over said thin layer of conductive material and terminating in quite a sharp apex positioned in line with the axis of said tubing.

5. An electronic tester as claimed in claim 1 having a temperature sensitive diode, said temperature sensitive diode connected to said detecting circuit for connection to a display for temperature, said temperature sensitive diode having pigtails connected to said substrate of said printed circuit board, said length of conductive tubing having a wall with a slot extending longitudinally from said end thereof, said substrate having a portion of a lateral edge to be positioned in said piece of tubing adjacent said slot in line therewith, said portion of said lateral edge having for each of said pigtails a mounting hole extending within said substrate substantially parallel to the sides thereof, a plated-through hole of said printed circuit board intersecting each of said mounting holes, said pigtails being inserted through said mounting holes for connecting said pigtails to respective plated-through holes and for positioning said temperature sensitive diode adjacent said slot and outside said tubing to be in close thermal contact with any fluid materials into which said probe is inserted.

* * * * *